United States Patent
Harrold

(10) Patent No.: US 6,901,810 B1
(45) Date of Patent: Jun. 7, 2005

(54) METHOD OF CYCLIC TESTING

(75) Inventor: David P. Harrold, Walled Lake, MI (US)

(73) Assignee: Williams International Co. L.L.C., Walled Lake, MI (US)

( * ) Notice: Subject to any disclaimer, the term of this patent is extended or adjusted under 35 U.S.C. 154(b) by 153 days.

(21) Appl. No.: 10/215,637

(22) Filed: Aug. 8, 2002

(51) Int. Cl.$^7$ .............................................. G01N 3/21
(52) U.S. Cl. ........................................................ 73/813
(58) Field of Search ........................ 73/809, 810, 812, 73/813, 814, 799, 804, 806, 808, 811

(56) References Cited

U.S. PATENT DOCUMENTS

| | | | |
|---|---|---|---|
| 3,228,237 A | | 1/1966 | Newton ......................... 73/88 |
| 3,763,698 A | | 10/1973 | Suzuki et al. ................ 73/88 R |
| 4,375,766 A | * | 3/1983 | Papay .......................... 73/809 |
| 4,397,714 A | * | 8/1983 | Janata et al. ................. 205/775 |
| 4,850,715 A | | 7/1989 | Gaffin .......................... 374/52 |
| 4,971,522 A | * | 11/1990 | Butlin .......................... 417/18 |
| 4,988,266 A | | 1/1991 | Nakamura et al. ........ 415/173.1 |
| 5,022,276 A | | 6/1991 | Thelen ....................... 73/865.3 |
| 5,167,159 A | * | 12/1992 | Lucking ................. 73/862.451 |
| 5,177,330 A | * | 1/1993 | Takahashi et al. ........... 200/5 A |
| 5,424,634 A | | 6/1995 | Goldfarb et al. .......... 324/158.1 |
| 6,044,713 A | | 4/2000 | Bassily ......................... 73/849 |
| 6,077,615 A | | 6/2000 | Yada et al. .................. 428/544 |
| 6,288,457 B1 | * | 9/2001 | Kako et al. .................. 307/119 |
| 6,439,030 B2 | * | 8/2002 | Suzuki et al. .............. 73/35.13 |
| 6,544,650 B2 | * | 4/2003 | Iwamoto ...................... 428/413 |

* cited by examiner

*Primary Examiner*—Max Noori
(74) *Attorney, Agent, or Firm*—Dinnin & Dunn, P.C.

(57) ABSTRACT

A part that is subject to at least a cyclic thermal stimulus is numerically simulated to determine extremum states of stress therein that would be suitable for an associated life cycle test. The assembly of the part in a fixture is then numerically simulated to determine a part holding condition by the fixture, and first and second test rotational speeds of the part and fixture as necessary to create states of stress in the part that are comparable to the extremum states of stress. The part is assembled in the fixture in accordance with the part holding condition, and the fixture and part are rotated in accordance with a control schedule by which the rotational speed thereof is isothermally cycled between the first and second test rotational speeds for a predetermined number of cycles so as to simulate a cyclic stress condition in the part that is representative of a life cycle test.

23 Claims, 4 Drawing Sheets

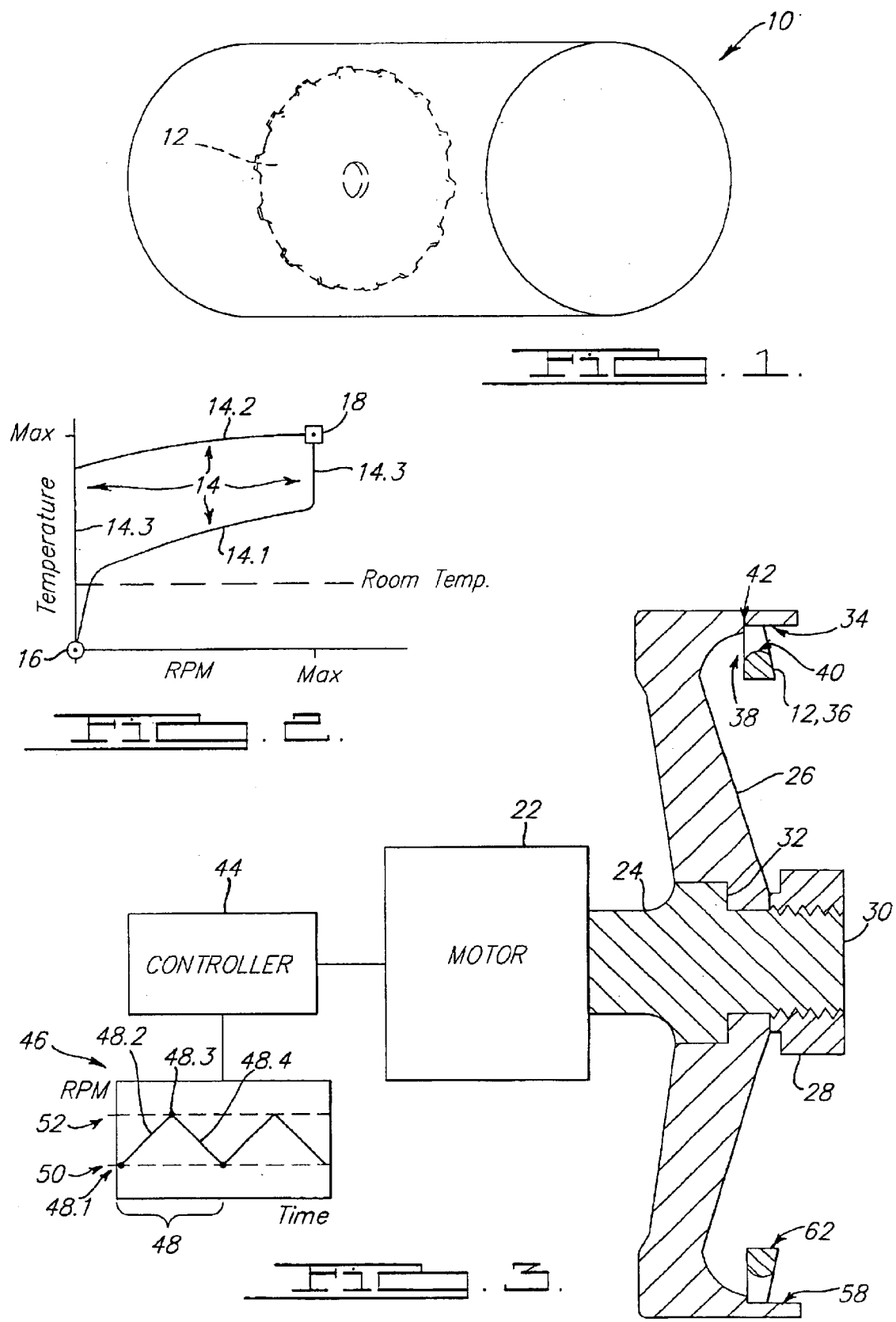

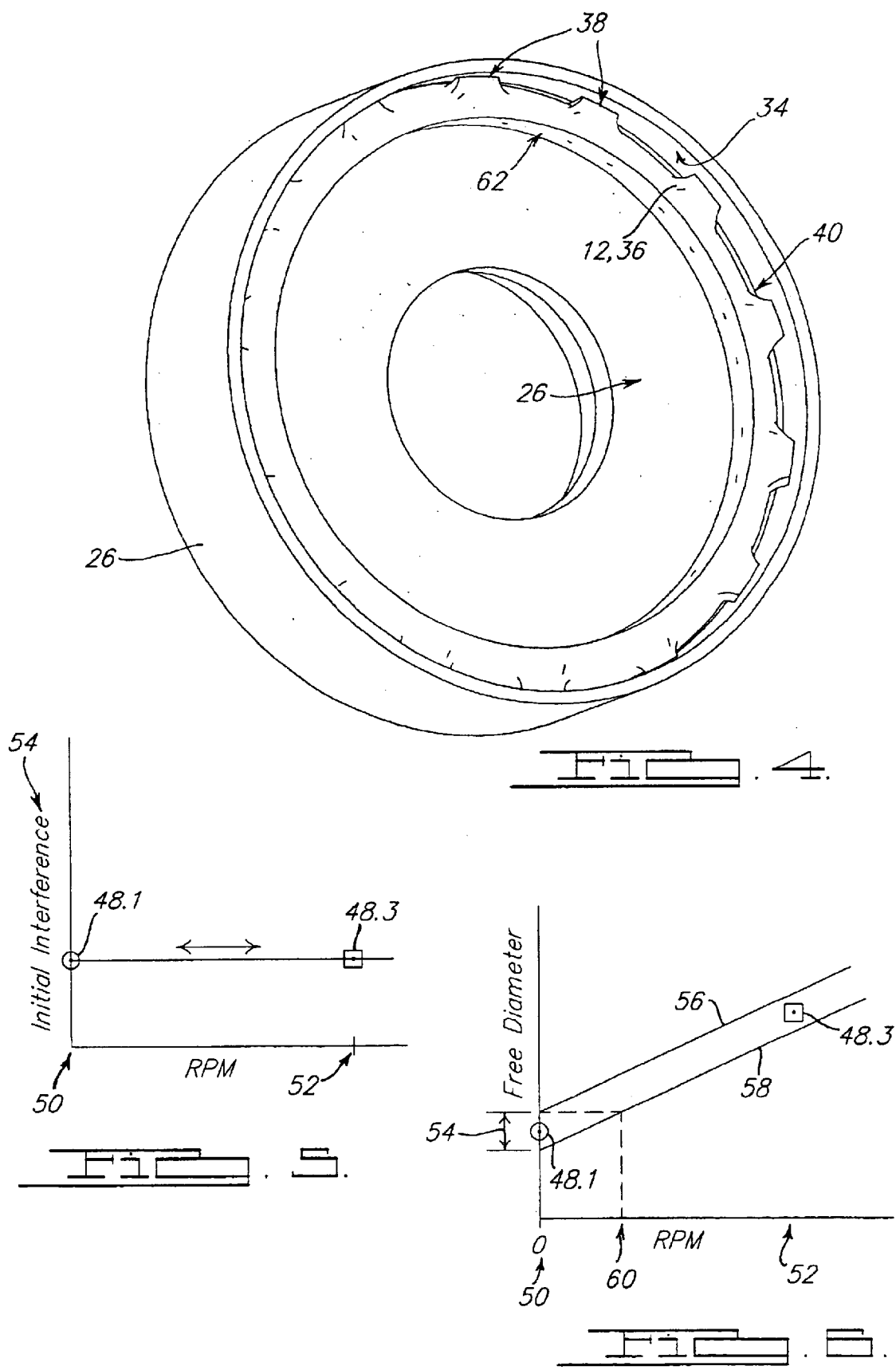

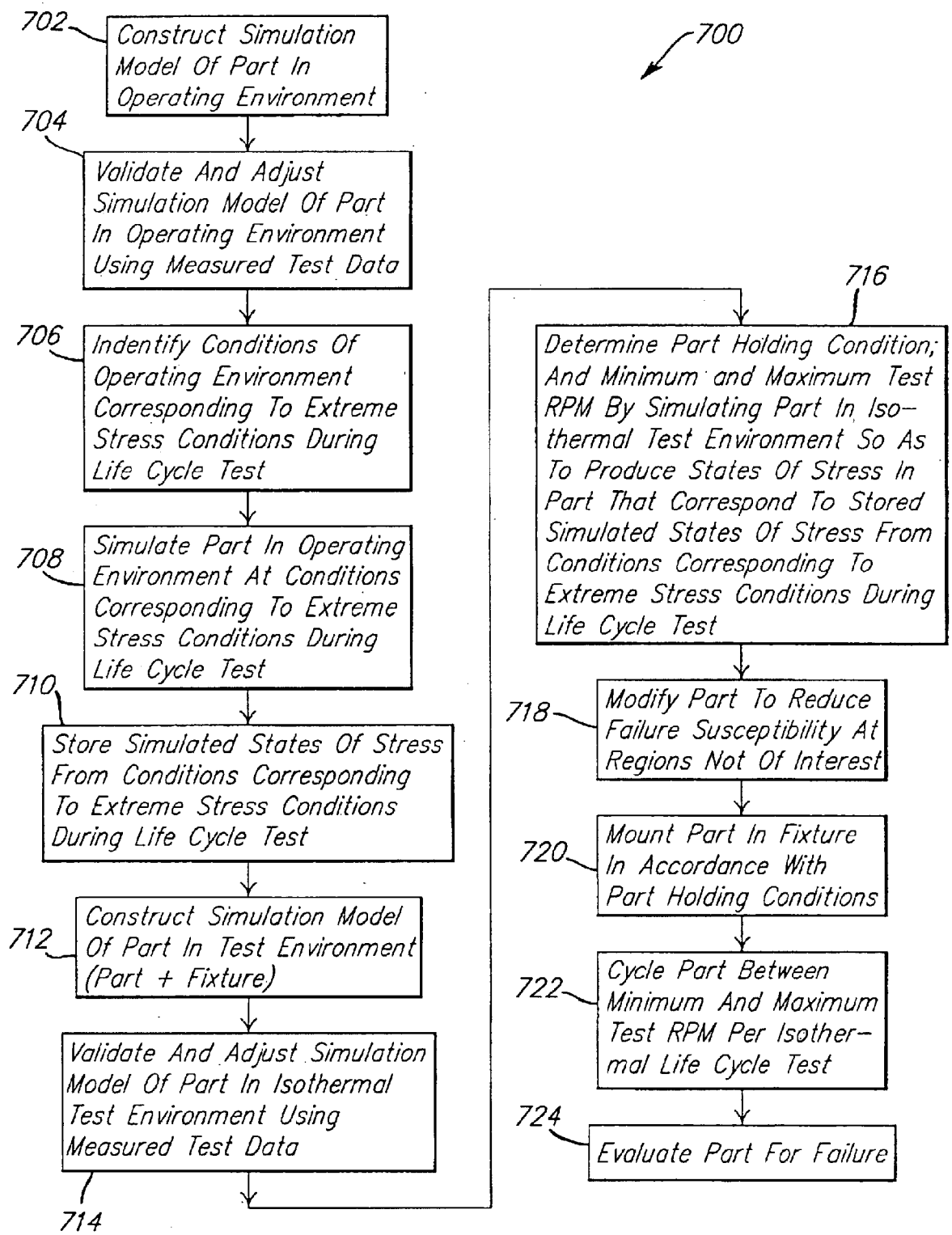

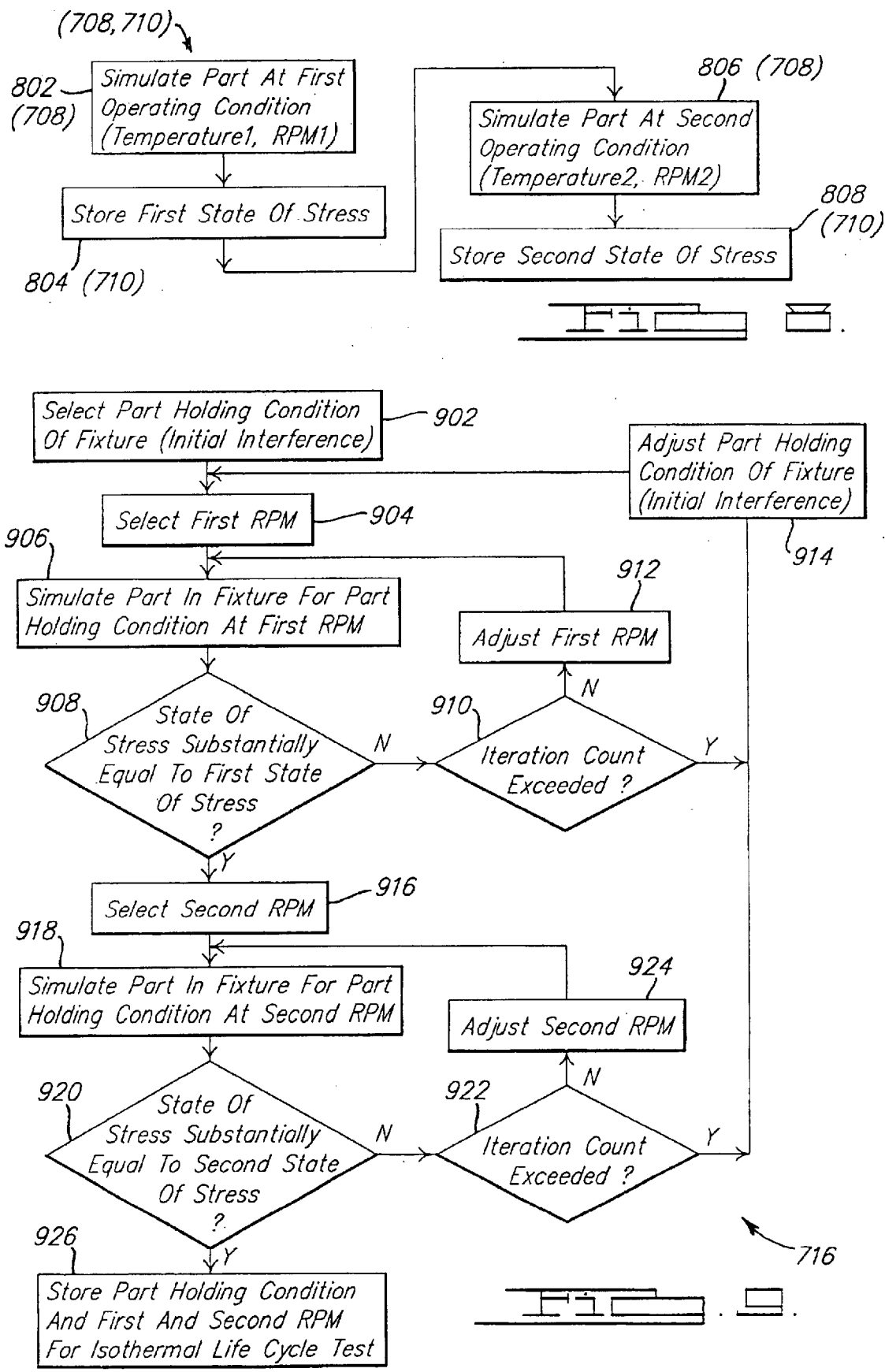

METHOD OF CYCLIC TESTING

STATEMENT REGARDING FEDERALLY SPONSORED RESEARCH OR DEVELOPMENT

The U.S. Government has a paid-up license in this invention and the right in limited cicumstances to require the patent owner to license others on reasonable terms as provided for by the terms of Contract No. DAAJ 09-91C-A004 awarded by the United States Army.

BRIEF DESCRIPTION OF THE DRAWINGS

In the accompanying drawings:

FIG. 1 illustrates a turbine engine comprising a rotor that is subject to thermal cyclic stress;

FIG. 2 illustrates various operating conditions of the rotor illustrated in FIG. 1;

FIG. 3 illustrates a system for performing an isothermal cyclic test of a portion of the rotor illustrated in FIG. 1;

FIG. 4 illustrates an isometric view of a rotor in a fixture in accordance with the system illustrated in FIG. 3;

FIG. 5 illustrates a diagram of a range of test conditions for the system illustrated in FIG. 3.

FIG. 6 illustrates the behavior of the rotor and fixture, responsive to rotational speed;

FIG. 7 illustrates a method of providing for simulating a cyclic state of stress in a part;

FIG. 8 illustrates a process of simulating a part in an operating environment corresponding to extreme stress conditions during an operating cycle; and FIG. 9 illustrates a process of determining parameters for an isothermal cyclic test.

DESCRIPTION OF EMBODIMENT(S)

Referring to FIG. 1, there is illustrated a turbine engine 10 comprising a rotor 12 that is subject to a range of temperatures and rotational speeds during the operational life thereof For example, referring to FIG. 2, the turbine engine 10 is designed to operate over a range of operating conditions with respect to the rotational speed (RPM) of the rotor 12, and the temperature of a particular portion thereof, within a particular boundary 14 as plotted in FIG. 2. For example, the lower boundary 14.1 corresponds to warm up from a cold soak condition, the upper boundary 14.2 corresponds to cool down from operation at maximum power, the left boundary 14.3 corresponds to a stationary condition, and the right boundary 14.4 corresponds to the maximum operating rotational speed. The state of stress within the rotor 12 is responsive to the associated temperature-rotational speed operating condition. For example, a cold, stationary rotor 12—as illustrated in FIG. 2 by a first operating condition 16 of temperature and rotational speed—would be exhibit a maximum compressive state of stress, whereas a hot, high speed rotor 12—as illustrated in FIG. 2 by a second operating condition 18 of temperature and rotational speed—would exhibit a maximum tensile state of stress. Over the life of the turbine engine 10, the temperature-rotational speed operating condition of the rotor 12 follows a trajectory from one condition to another and may cycle back and forth between operating conditions, e.g. between a stationary cold condition, i.e. the first operating condition 16, and a maximum power condition, i.e. the second operating condition 18. Over time, this cyclic operation can cause a fatigue failure of the material of the rotor 12 if the rotor 12 is not otherwise adapted to mitigate thereagainst, for example, by designing the rotor 12 to successfully pass an accelerated life cycle test of the turbine engine 10 by which the turbine engine 10 is operated so as to repeatedly cycle between the first 16 and second 18 operating conditions with respect to temperature and rational speed. However, an accelerated life cycle test would involve running the turbine engine 10 over a series of different operating conditions for sufficient time at each operating condition to allow for sufficient heat transfer to allow the parts of the turbine engine 10 to heat or cool sufficiently, and for a sufficient number of cycles to simulate the operating life of the turbine engine 10. Accordingly, an accelerated life cycle test can be relatively time consuming and relatively expensive.

Referring to FIGS. 3 and 4, a cyclic test apparatus 20 is illustrated by which the rotor 12, or a pertinent portion thereof, can be isothermally subjected to a cyclic stress condition that is substantially comparable to an associated cyclic stress condition that the rotor 12 would be subjected to in the above-described accelerated life cycle test, but in a substantially shorter period of time than would be required for the associated accelerated life cycle test. The cyclic test apparatus 20 comprises a motor 22 with an arbor 24 to which is mounted a fixture 26, for example with a nut 28 threaded on the end 30 of the arbor 24. Whereas FIG. 3 illustrates the fixture 26 secured to the arbor 24 by compression between a shoulder 32 of the arbor 24 and the nut 28, the fixture 26 could also be either tapered, keyed or splined to the arbor 24 so as to be more positively engaged thereby. The fixture 26 comprises an inside surface 34 that is adapted to mate with the outside surface of a part 36—e.g. a rotor 12 of a turbine engine 10—to be tested. More particularly, the inside diameter of the inside surface 34 is sufficiently smaller than outside diameter of the part 36/rotor 12 so that the part 36/rotor 12 is held securely therein by an interference fit therewith. More particularly, the part 36/rotor 12 illustrated in FIGS. 3 and 4 comprises a plurality of tip portions 38 that contact the inside surface 34 of the fixture 26. The interference fit compresses the part 36/rotor 12 sufficiently so as to simulate the state of stress in the rotor 12, at a location 40 thereof to be simulated, for example, corresponding to an associated temperature-rotational speed condition (first operating condition 16) that would result in a similar compressive state of stress as a result of a cold soak condition of the turbine engine 10. The part 36/rotor 12 is aligned against an inside shoulder 42 abutting the inside surface 34 of the fixture 26.

In operation, the part 36 is installed in the fixture 26, for example, by pressing the part 36 in the fixture 26; or by first either thermally expanding the fixture 26, or thermally shrinking the part 36 before placing the part 36 in the fixture 26. The fixture 26 is then mounted on the arbor 24 and secured thereon with the nut 28, after which the part 36 is tested by controlling the speed of the motor 22 with a controller 44 in accordance with a control schedule 46 of rotational speed (RPM) as a function of time over a predetermined number of cycles 48. For example, each cycle 48 comprises a first segment or operating point 48.1 comprising operation at a first rotational speed 50, a second segment 48.2 comprising a ramped increase in rotational speed to a second rotational speed 52, a third segment or operating point 48.3 comprising operation at the second rotational speed 52, and a fourth segment 48.4 comprising a ramped decrease in rotational speed to the first rotational speed 50.

Referring to FIG. 5, the parameters of the test comprise initial interference 54 and test rotational speed, wherein the initial interference 54 is the amount of interference between the part 36 and the inside surface 34 of the fixture 26. After installation of the part 36 in the fixture 26, the part 36 and fixture 26 are cycled between the first rotational speed 50, e.g. having a predetermined value of substantially zero RPM, and the second rotational speed 52, e.g. having a predetermined value that is determined in accordance with a process described hereinbelow.

Referring to FIG. 6, there are illustrated plots of the outside diameter 56 of the part 36 and inside diameter 58 of the inside surface 34 of the fixture 26, each as a function of rotational speed (RPM). The diameters plotted in FIG. 6 are the free diameters of the associated components, i.e. with the components not assembled with one another. Accordingly, since the outside diameter 56 of the part 36 is greater than the inside diameter 58 of the inside surface 34 of the fixture 26, then when assembled, the part 36 would have an interference fit with the inside diameter 58 of the inside surface 34 of the fixture 26, and therefore be secured thereto thereby. Both the part 36 and the fixture 26 expand with increasing rotational speed as a result of associated centrifugal force, and the material(s) and structure of the fixture 26 are selected so as to expand at about the same rate with respect to rotational speed (RPM) as does the part 36 so that the part 36 is continuously in interference with, and therefor secured to, the fixture 26 throughout the range of rotational speeds in the control schedule 46. As illustrated in FIG. 6, at the first rotational speed 50 the free inside:diameter 58 of the inside surface 34 of the fixture 26 is less than the free outside diameter 56 of the part 36, so that when assembled in the fixture 26, the part 36 exhibits a compressive state of stress. As the rotational speed of the fixture 26/part 36 is increased, both the part 36 and the fixture 26 expand but the part 36 continues to exhibit a compressive state of stress until a transitional rotational speed 60 is reached, at which point the inside diameter 58 of the inside surface 34 of the rotating fixture 26 would be equal to the free outside diameter 56 of the part 36 if the part 36 were stationary. Accordingly, at the transitional rotational speed 60, the part 36 is substantially unstressed. As the rotational speed of the fixture 26/part 36 is further increased, the part 36 is further expanded by centrifugal force so that the part 36 then exhibits a tensile state of stress. The initial interference 54, first rotational speed 50, and second rotational speed 52 are adapted so that the state of stress in the part 36 in the fixture 26 at the first rotational speed 50 is comparable to the compressive state of stress in the part at the first operating condition 16 of temperature and rotational speed, and so that state of stress in the part 36 in the fixture 26 at the second rotational speed 52 is comparable to the compressive state of stress in the part at the second operating condition 18 of temperature and rotational speed.

Referring to FIG. 7, in accordance with a method 700 of providing for simulating a cyclic state of stress in a part 36, the part 36 to be tested is first numerically simulated in its anticipated operating environment in order to determine the anticipated extremum of the cyclic state of stress (steps 702, 704, 706, 708 and 710), and then the part 36 and fixture 26 are numerically simulated to determine the initial interference 54, first rotational speed 50, and second rotational speed 52 that provide for isothermal states of stress in the part 36 that are comparable to the anticipated extremum of the cyclic state of stress determined from the first numerical simulation (steps 712, 714 and 716), after which the part 36 is prepared and secured to the fixture 26 by the initial interference 54, cycled for a predetermined number of cycles between the first rotational speed 50 and the second rotational speed 52, and then evaluated for evidence of resulting fatigue failure (steps 718, 720, 722 and 724).

More particularly, beginning with step (702), a numerical simulation model is constructed of the part 36 in its intended operating environment. The numerical simulation model is intended to provide a simulation of the stress and strain within the part 36 responsive to the thermal and dynamic (e.g. rotation speed) properties of the operating environment. For example, commercially available numerical simulation programs are well known that utilize the Finite Element Method (FEM) in accordance with fundamental mechanical and thermal physical relationships to predict the state of stress and strain in a simulated part responsive to simulated physical and thermal stimuli. Examples of commercially available numerical simulation programs include ANSYS by Swanson Analysis Systems, Inc. located in Houston, Pa.; and NASTRAN by MacNeal-Schwindler corporation in San Fernando, Calif. After construction, and if possible, in step (704), the finite element model of the part 36 is validated and adjusted using measured test data from the part 36 in the actual operating environment.

Then, in step (706), the conditions of the anticipated operating environment are identified that would result in extremum in the state of stress of the part 36. For example, the minimum cold soak temperature would be identified as a condition that would result in an extremum of compressive stress, and the maximum operating temperature and rotational speed would be identified as a condition that would result in an extremum of tensile stress.

In step (708), the part 36 is simulated with the finite element model developed in steps (702) and (704) in accordance with conditions identified in step (706) that would be appropriate for an associated life cycle test of the part 36, and, in step (710), the resulting states of stress at the extremum stress conditions are stored for future use. More particularly, referring to FIG. 8, in step (802), the part 36 is simulated at a first operating condition (i.e. first operating condition 16) comprising a first temperature and an associated first operational rotational speed, and in step (804) the resulting first state of stress is stored for future use. Similarly, in step (806), the part 36 is simulated at a second operating condition (i.e. second operating condition 18) comprising a second temperature and an associated second operational rotational speed, and in step (808) the resulting second state of stress is stored for future use.

Returning to FIG. 7, following step (710), a finite element numerical simulation model of the part 36 and fixture 26 are constructed in step (712), e.g. in accordance with the same numerical simulation program as used for step (702). Then, in step (714), the finite element model may be validated and adjusted using measured data from the part 36 in an isothermal test environment. Then, in step (716), the part 36 and fixture 26 are simulated with the finite element model developed in steps (712) and (714) so as to determine the part holding condition (e.g. initial interference 54), the first rotational speed 50 and the second rotational speed 52 that will produce respective states of stress in the part 36 that corresponding to the states of stress stored in steps (804) and (808) respectively, for the part 36 and fixture 26 at the isothermal test temperature.

For example, the fatigue strength of a particular material is typically temperature dependent, so that the isothermal test temperature would be selected so as to correspond to the maximum intended operating temperature of the rotor 12 in the turbine engine 10, e.g. about 1200 degrees Fahrenheit, so that the part 36 exhibits a fatigue susceptibility that is similar to that when operated in its worst case intended operating environment.

More particularly, referring to FIG. 9, in step (902), a part holding condition is initialized, wherein the part holding condition is the means by which the part 36 is held in the fixture 26, and can be used as a means to initially compress the part 36. For example, the part holding condition may comprise an initial interference 54 between the outside diameter 56 of the part 36 and the inside diameter 58 of the inside surface 34 of the fixture 26. Alternately, the part holding condition may comprise an associated clamping or holding force that would cause an associated initial state of stress in the part 36.

Then, the first rotational speed 50 is selected, i.e. estimated, in step (904), and in step (906) the part 36 and fixture 26 assembly are simulated at the associated first rotational speed 50 and an associated isothermal test temperature so as to determine an associated state of stress of the part 36, which, in step (908), is compared with the first state of stress stored in step (804). If the state of stress from step (906) is substantially different from the first state of stress stored in step (804), then either the first rotational speed 50 is adjusted in step (912) if an iteration count has not been exceeded in step (910), or the part holding condition (e.g. initial interference 54) is adjusted in step (914). Typically, the first rotational speed 50 would be set to a value of zero, thereby precluding the option of its adjustment in step (912), so that the part holding condition would be adjusted in step (914) in order to satisfy the condition of step (908). The process is repeated beginning with step (906) until the condition of step (908) is satisfied.

After the condition of step (908) is satisfied, then the second rotational speed 52 is selected, i.e. estimated, in step (916), and, in step (918), the part 36 and fixture 26 assembly are simulated at the associated second rotational speed 52 and an associated isothermal test temperature so as to determine an associated state of stress of the part 36, which, in step (920), is compared with the second state of stress stored in step (808). If the state of stress from step (918) is substantially different from the second state of stress stored in step (808), then the second rotational speed 52 is adjusted in step (924) if an iteration count has not been exceeded in step (922). If the iteration count is exceeded in step (922), then the part holding condition is adjusted in step (914), and the above-described process repeats with step (904). Otherwise, after the condition of step (920) is satisfied, then, in step (926), the part holding condition (e.g. initial interference 54), the first rotational speed 50, and the second rotational speed 52 are stored for used in a subsequent isothermal life cycle test of the part 36.

Returning to FIG. 7, following step (716)/(926), in step (718), the part 36 to be tested may be modified as necessary to reduce failure susceptibility at regions not of interest. For example, the inside diameter 62 of the rotor 12 illustrated in FIGS. 3 and 4 has been adapted, e.g. machined, so that this surface, which is not in a particular region of interest of the rotor 12, does not otherwise become susceptible to fatigue failure during the isothermal life cycle test. The finite element numerical simulation model of the part 36 and fixture 26 can be used to identify regions of the part 36 that could be susceptible to fatigue failure as a result of an isothermal life cycle test, but which would otherwise not likely be susceptible to fatigue failure in the intended operating environment.

Following step (718), in step (720), the part 36 is mounted in the fixture 26 in accordance with the part holding condition identified in step (716). Then, in step (722), the part 36 and fixture 26 assembly is rotated by the motor 22 in accordance with a control schedule 46 comprising a predetermined number of cycles of an isothermal life cycle test, each cycle of which comprising a schedule of rotational speed that varies between the first 56 and second 58 test rotational speeds—identified in step (716)—as a function of time. The isothermal life cycle test provides for a cyclic variation of stress in the part 36 that is comparable to the variation in stress caused by variations in both temperature and rotational speed in the intended operating environment, but which can be produced relatively quickly by changes in rotational speed without the delays that would otherwise be required for associated thermal cycles. Alternately, the temperature may also be varied over the duration of the life cycle test, e.g. from one group of cycles to another, so as to generate other cyclic states of stress in the part 36.

Generally, a part 36 that is subject to thermal cyclic stress in an operating environment may be designed in accordance with a process that incorporates the above described method 700 of providing for simulating a cyclic state of stress in an analog of the part 36. For example, after the part is initially designed, an analog thereof, e.g. either a prototype, production prototype, or production sample of the part 36, or a modified version thereof in accordance with step (718) of the method 700, may be tested in accordance with the method 700 so as to verify the suitability of the design of the part 36 responsive to thermally or combined thermally and dynamically induced cyclic states of stress that could otherwise induce fatigue failure therein. After qualifying the design of the part 36 by testing an analog thereof using the above-described method 700, then the part 36 can be produced in accordance with the qualified design, with increased confidence that the part 36 will likely not be subject to fatigue failure during the operation thereof in its intended environment Accordingly, the method 700 provides for reducing the duration of the design cycle for parts that can be subject to thermally or combined thermally and dynamically induced cyclic states of stress during operation thereof.

While specific embodiments have been described in detail in the foregoing detailed description and illustrated in the accompanying drawings, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the fill breadth of the appended claims and any and all equivalents thereof.

I claim:

1. A method of simulating a cyclic state of Stress in a part, comprising:
 a. installing a par to be tested within a fixture that is adapted to bold said part;
 b. subjecting said fixture to a rotational speed that is greater than or equal to zero; and
 c. varying said rotational speed in accordance with a cyclic pattern, wherein said cyclic pattern comprises a number of cycles, each cycle of said number of cycles comprising
   i. a first rotational speed related to a first state of stress; and
   ii. a second rotational speed related to a second state of stress, wherein said second rotational speed is greater than said fist rotational speed, said first state of stress corresponds to a first thermal condition of said part, said second state of stress corresponds to a second thermal condition of said part, and said number of cycles are representative of at least a portion of an expected lifetime of said part under conditions in which said part is intended to be used.

2. A method of simulating a cyclic state of stress in a part as recited in claim 1, wherein said fixture comprises an inner diameter that is adapted to mate with an outer diameter of said part in accordance with an interference fit when said part and said fixture am stationary.

3. A method of simulating a cyclic state of stress in a part as recited in claim 1, wherein said first rotational speed comprises a minimum speed of said cycle.

4. A method of simulating a cyclic state of stress in a part as recited in claim 3, wherein said minimum speed is substantially equal to zero.

5. A method of simulating a cyclic state of stress in a part as recited in claim 1, wherein said first state of stress is compressive in at least one direction.

6. A method of simulating a cyclic state of stress in a part as recited in claim 1, wherein said second rotational speed comprises a maximum speed of said cycle.

7. A method of simulating a cyclic state of stress in a part as recited in claim 1, wherein said second state of stress is compressive in at least one direction.

8. A method of simulating a cyclic state of stress in a part as recited in claim 1, wherein said fixture is adapted to securely hold said part at all rotational speed conditions of said cycle.

9. A method of simulating a cyclic state of stress in a part as recited in claim 1, further comprising evaluating said part following completion of said number of cycles for the existence of a condition indicative of a failure of said part.

10. A method of simulating a cyclic state of stress in a part as recited in claim 1, further comprising adapting said part prior to commencing said cyclic pattern so that a portion of said part is not subject to failure responsive to said cyclic pattern.

11. A method of providing for simulating a cyclic state of stress in a part, comprising:
  a. performing a first numerical simulation of said part under a first simulation condition that is representative of a first operating condition in which said part may be used;
  b. performing a second numerical simulation of said part under a second simulation condition that is representative of a second operating condition in which said part may be used, wherein said first and second operating conditions result in different associated thermally induced states of stress in said part;
  c. performing a third numerical simulation of said part under a third simulation condition that is representative of a said part held by a test fixture in accordance with a holding condition and rotated at a first rotational speed that is greater than or equal to zero;
  d. performing a fourth numerical simulation of said part under a fourth simulation condition that is representative of a said part held by said test fixture in accordance with said holding condition and rotated at a second rotational speed that is greater than said first rotational speed;
  e. repeating said third or said first numerical simulations for different combinations of said holding condition, said first Rotational speed and said second rotational speed as necessary to determine said holding condition, said first rotational speed and said second rotational speed so that said third simulation condition results in a state of stress in said part that is substantially close to a state of stress in said part under said first simulation condition, and said fourth simulation condition results in a state of stress in said part that is substantially close to a state of stress in said part under said second simulation condition;
  f. providing for assembling said part with a fixture that is adapted to hold said part in accordance with said holding condition; and
  g. providing for subjecting said fixture to a cyclic pattern of rotational speed comprising a number of cycles, wherein each cycle comprises both said first rotational speed and said second rotational speed.

12. A method of providing for simulating a cyclic state of stress in a part as recited in claim 11, wherein said different associated states of stress a representative of corresponding extremes of a cyclic state of stress.

13. A method of providing for simulating a cyclic state of stress in a part as recited in claim 11, wherein said first rotational speed substantially corresponds to a minimum rotational speed of said cycle and said second rotational speed substantially corresponds to a maximum rotational speed of said cycle.

14. A part that is subject to thermal cyclic stress in an operating environment, wherein said part is designed in accordance with a process that incorporates a method of simulating a cyclic state of stress in an analog of the part, said method comprising:
  a. installing the analog of the part to be tested within a fixture that is adapted to hold said analog of the part;
  b. subjecting said fixture to a rotational speed that is greater than or equal to zero; and
  c. varying said rotational speed in accordance with a cyclic pattern, wherein said cyclic pattern comprises a number of cycles, each cycle of said number of cycles comprising
    i. a first rotational speed related to a first state of stress; and
    ii. a second rotational speed related to a second state of stress, wherein said second rotational speed is greater than said first rotational speed, said first state of stress corresponds to a first thermal condition of said analog of the part, said second state of stress corresponds to a second thermal condition of said analog of the part, and said number of cycles are representative of at least a portion of an expected lifetime of said analog of the part under conditions in which said analog of the part is intended to be used.

15. A part as recited in claim 14, wherein said fixture comprises an inner diameter that is adapted to mate with an outer diameter of said analog of the part in accordance with an interference fit when said analog of the part and said fixture are stationary.

16. A part as recited in claim 14, wherein said first rotational speed comprises a minimum speed of said cycle.

17. A part as recited in claim 16, wherein said minimum speed is substantially equal to zero.

18. A part as recited in claim 14, wherein said first state of stress is compressive in at least one direction.

19. A part as recited in claim 14, wherein said second rotational speed comprises a maximum speed of said cycle.

20. A part as recited in claim 14, wherein said second state of stress is compressive in at least one direction.

21. A part as recited in claim 14, wherein said fixture is adapted to securely hold said analog of the part at all rotational speed conditions of said cycle.

22. A part as recited in claim 14, further comprising evaluating said analog of the part following completion of said number of cycles for the existence of a condition indicative of a potential failure of said analog of the part.

23. A part as recited in claim 14, further comprising adapting said analog of the part prior to commencing said cyclic pattern so that a portion of said analog of the part is not subject to failure responsive to said cyclic pattern.

* * * * *

UNITED STATES PATENT AND TRADEMARK OFFICE
CERTIFICATE OF CORRECTION

PATENT NO. : 6,901,810 B1
DATED : June 7, 2005
INVENTOR(S) : David P. Harrold

It is certified that error appears in the above-identified patent and that said Letters Patent is hereby corrected as shown below:

Column 3,
Line 26, please delete ":" after "the free inside".

Column 4,
Line 14, please delete "Pa" and insert -- Pennsylvania -- after "Houston".

Column 6,
Line 42, please delete "Stress" and insert -- stress -- after "cyclic state".
Line 44, please delete "par" and insert -- part -- after "installing a".
Line 45, please delete "bold" and insert -- hold -- after "adapted to".
Line 56, please delete "fist" and insert -- first -- after "greater than said".

Column 7,
Line 54, please delete "Rotational" and insert -- rotational -- after "said first".

Signed and Sealed this

Thirteenth Day of December, 2005

JON W. DUDAS
*Director of the United States Patent and Trademark Office*